US00PP12958P2

(12) United States Plant Patent
Strijbis

(10) Patent No.: US PP12,958 P2
(45) Date of Patent: Sep. 17, 2002

(54) CHRYSANTHEMUM PLANT NAMED 'DARK REGAL YODAVIS'

(75) Inventor: Jan Strijbis, De Lier (NL)

(73) Assignee: Yoder Brothers, Inc., Barberton, OH (US)

( * ) Notice: Subject to any disclaimer, the term of this patent is extended or adjusted under 35 U.S.C. 154(b) by 42 days.

(21) Appl. No.: 09/594,756

(22) Filed: Jun. 16, 2000

(51) Int. Cl.[7] ..... A01H 5/00
(52) U.S. Cl. ..... Plt./286
(58) Field of Search ..... Plt./286, 297

(56) References Cited

U.S. PATENT DOCUMENTS

PP8,292 P * 7/1993 VandenBerg ..... Plt./286

OTHER PUBLICATIONS

UPOV–ROM, 2001/04, Plant Variety Database, GTI Jouve Retrieval Software, 3 citations for 'Dark Regal Yodavis'.*
Copy of paper confirming Nov. 5, 1996 filing date for QZ PBR 961214 and Feb. 14, 2000 Grant date for resulting Grant #5804.*

* cited by examiner

*Primary Examiner*—Howard J. Locker
(74) *Attorney, Agent, or Firm*—C A. Whealy

(57) ABSTRACT

A distinct cultivar of Chrysanthemum plant named 'Dark Regal Yodavis', characterized by its upright, outwardly spreading and uniformly mounded plant habit; freely branching habit; uniform flowering response; nine-week response time; floriferousness; daisy-type inflorescences that are about 5.7 cm in diameter; dark purple-colored ray florets with bright yellow disc florets; good winter production performance; and good postproduction longevity with inflorescences maintaining good substance and color for about three weeks in an interior environment.

1 Drawing Sheet

BACKGROUND OF THE INVENTION

The present Invention relates to a new and distinct cultivar of Chrysanthemum plant, botanically known as *Dendranthema grandiflora* and hereinafter referred to by the cultivar name Dark Regal Yodavis.

The new Chrysanthemum was discovered by the Inventor in April, 1996, in a controlled environment in De Lier, The Netherlands, as a naturally-occurring branch mutation of the *Dendranthema grandiflora* 'Regal Davis', disclosed in U.S. Plant Pat. No. 8,292. The branch mutation was observed on a single plant in a group of flowering plants of the parent cultivar. The selection of this plant was based on its different ray floret color. Compared to plants of the parent cultivar, Regal Davis, plants of the new Chrysanthemum have darker purple-colored ray florets and slightly larger inflorescences.

Asexual reproduction of the new Chrysanthemum by vegetative tip cuttings was first conducted in De Lier, The Netherlands, in May, 1996. Asexual reproduction by cuttings has shown that the unique features of this new Chrysanthemum are stable and reproduced true to type in successive generations.

SUMMARY OF THE INVENTION

The cultivar Dark Regal Yodavis has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dark Regal Yodavis'. These characteristics in combination distinguish 'Dark Regal Yodavis' as a new and distinct Chrysanthemum:

1. Upright, outwardly spreading and uniformly mounded plant habit.
2. Freely branching, dense and full plants.
3. Uniform flowering response.
4. Nine-week response time.
5. Very freely flowering.
6. Daisy-type inflorescences that are about 5.7 cm in diameter.
7. Dark purple-colored ray florets with bright yellow disc florets.
8. Can be grown as a natural spray-type.
9. Good winter production performance.
10. Good postproduction longevity with inflorescences maintaining good substance and color for about three weeks in an interior environment.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the sheet comprises a top perspective view of a typical flowering plant of 'Dark Regal Yodavis'.

The photograph at the bottom of the sheet comprises a close-up view of typical inflorescences of the cultivar Dark Regal Yodavis.

DETAILED BOTANICAL DESCRIPTION

In the following description, color references are made to The Royal Horticultural Society Colour Chart except where general terms of ordinary dictionary significance are used. The following observations and measurements describe plants grown and flowered during the Spring in Salinas, Calif. and Leamington, Ontario, Canada, under greenhouse conditions which approximate those generally used in commercial potted Chrysanthemum production. Four unrooted cuttings were directly stuck in a 15-cm container and pinched once. Plants used for this description were grown as spray-types. Measurements and numerical values represent averages of typical flowering plants.

Botanical classification: *Dendranthema grandiflora* cultivar Dark Regal Yodavis.

Commercial classification: Daisy-type potted Chrysanthemum.

Parentage: Naturally-occurring branch mutation of *Dendranthema grandiflora* cultivar Regal Davis, disclosed in U.S. Plant Pat. No. 8,292.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy-type potted Chrysanthemum which can be grown as a natural spray-type. Inverted triangle; stems upright and outwardly spreading giving a uniformly mounted appearance to the plant. Freely branching, about four lateral branches develop after removal of terminal apex (pinching); dense and full plants. Moderately vigorous.

*Plant height.*—About 20 cm.

*Plant width.*—About 37 cm.

*Lateral branches.*—Length: About 11 cm. Diameter: About 3 mm. Internode length: About 1.2 cm. Strength: Strong, flexible. Texture: Pubescent. Color: 144A.

*Foliage description.*—Arrangement: Alternate. Length: About 5.5 cm. Width: About 4.1 cm. Apex: Cuspidate. Base: Mostly attenuate. Margin: Palmately lobed, sinuses between lateral lobes divergent to parallel. Texture: Upper and lower surfaces with very fine pubescence; veins prominent on lower surface. Color: Young foliage upper surface: 147A. Young foliage lower surface: 147B. Mature foliage upper surface: 147A. Mature foliage lower surface: 147B. Venation upper surface: 147B. Venation lower surface: 147B. Petiole length: About 2.7 cm. Petiole diameter: About 2 mm. Petiole color: Close to 147B.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about nine weeks later.

*Postproduction longevity.*—Inflorescences maintain good color and substance for about three weeks in an interior environment.

*Quantity of inflorescences.*—Typically grown as a spray-type; about five to six inflorescences per lateral stem, about 20 to 24 inflorescences per plant.

*Inflorescence bud.*—Height: About 6 mm. Diameter: About 7 mm. Color: Darker than 143A.

*Inflorescence size.*—Diameter: About 5.7 cm. Depth (height): About 1.3 cm. Diameter of disc: About 1.6 cm. Receptacle diameter: About 6 cm.

*Ray florets.*—Shape: Elongated-oblong. Orientation: Slightly upright, about 20° from perpendicular to peduncle. Aspect: Straight and flat. Length: About 2.6 cm. Width: About 9 mm. Apex: Acute, mammilate or dentate. Base: Attenuate; short to medium corolla tube. Margin: Entire. Texture: Smooth, glabrous, satiny. Number of ray florets per inflorescence: About 23; two rows. Color: When opening, upper surface: Close to 61A to 71A. When opening, lower surface: Close to 70D, heavily overlain darker purple, close to 70A, longitudinal stripes. Fully opened, upper surface: Richer purple than 61A to close to 71A; fading to 70A to 70B heavily overlain with 61A to 71A. Fully opened, lower surface: Close to white especially at base and heavily overlain with purple, 70A to 70B, longitudinal stripes.

*Disc florets.*—Shape: Tubular, elongated. Apex: Five-pointed. Length: About 6 mm. Width: Apex, about 1.5 mm; base, about 1 mm. Number of disc florets per inflorescence: About 120. Color: Immature: Close to 144A. Mature: Apex: 5A. Mid-section: Close to 154C. Base: 155D.

*Peduncles.*—Length: First peduncle: About 1.6 cm. Fourth peduncle: About 4.5 cm. Diameter: About 1.5 mm. Angle to vertical: About 50° from vertical. Strength: Strong, flexible. Color: 144A.

*Reproductive organs.*—Androecium: Present on disc florets only. Anther color: 154A to 9A. Pollen amount: Scarce. Pollen color: 12A to 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Dark Regal Yodavis', as illustrated and described.

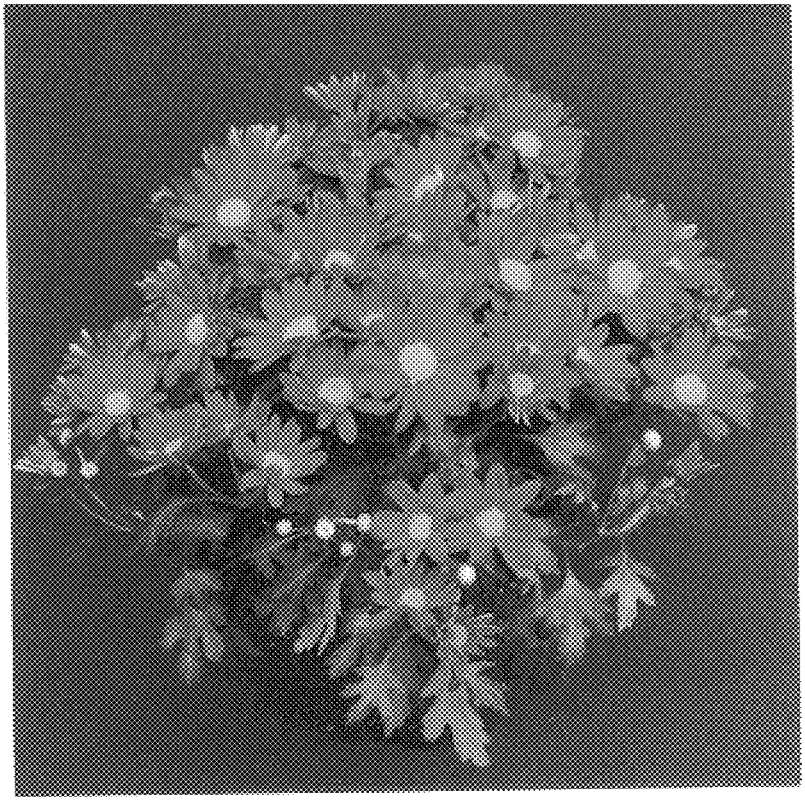
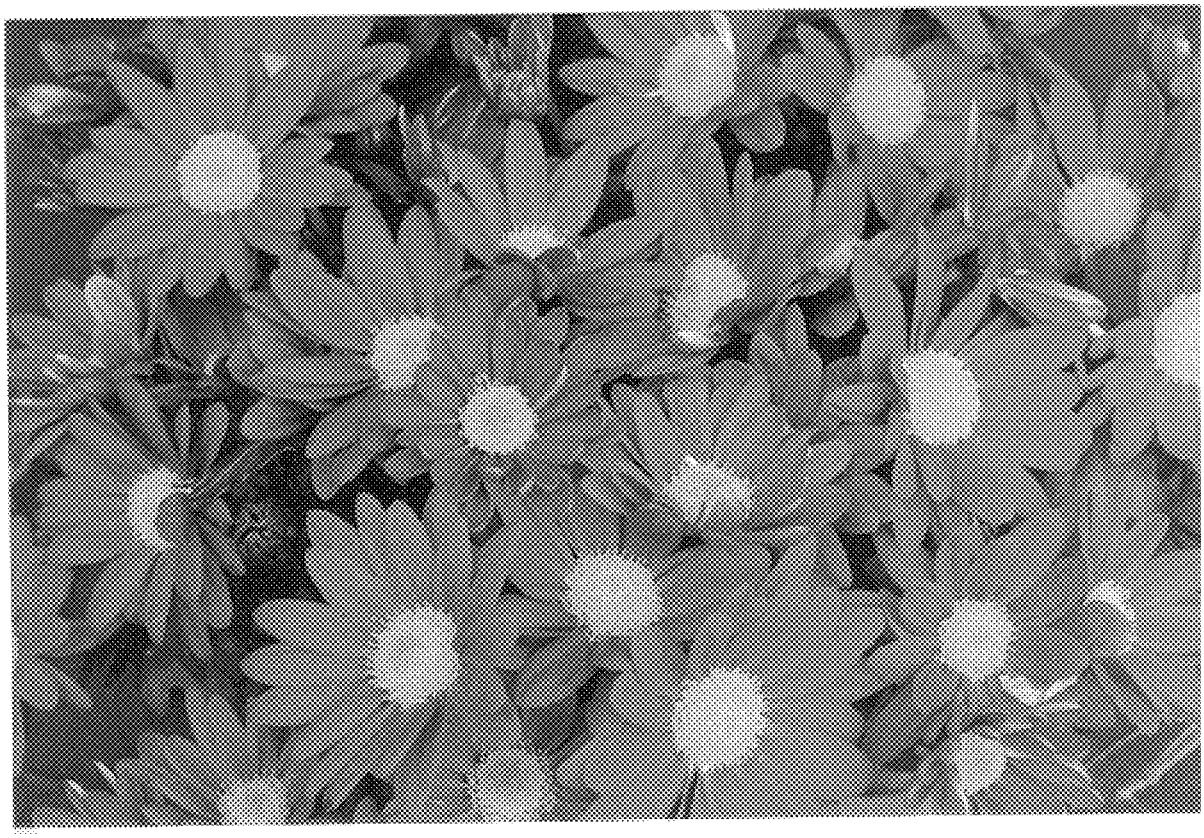

* * * * *